United States Patent [19]

Rauber

[11] Patent Number: 4,766,253

[45] Date of Patent: Aug. 23, 1988

[54] PROCESS FOR PREPARING CHLORINATED DIPHENYL ETHERS

[75] Inventor: Peter Rauber, Thürnen, Switzerland

[73] Assignee: Ciba-Geigy Corporation, Ardsley, N.Y.

[21] Appl. No.: 46,594

[22] Filed: May 4, 1987

[51] Int. Cl.[4] .................. C07C 41/16; C07C 43/275; C07C 43/29

[52] U.S. Cl. ................................................ 568/639

[58] Field of Search ........................................ 568/639

[56] References Cited

U.S. PATENT DOCUMENTS

| | | | |
|---|---|---|---|
| 3,371,120 | 2/1968 | Nowotny | 568/639 |
| 3,472,782 | 10/1969 | Nowotny | 568/639 |
| 4,266,082 | 5/1981 | Cöllin et al. | 568/639 |
| 4,289,909 | 9/1981 | Freenor, III et al. | 568/639 |
| 4,349,487 | 9/1982 | Renga | 568/639 |

FOREIGN PATENT DOCUMENTS

| | | | |
|---|---|---|---|
| 0021868 | 1/1981 | European Pat. Off. | 568/639 |
| 0024019 | 2/1981 | European Pat. Off. | 568/639 |
| 0051235 | 2/1982 | European Pat. Off. | 568/639 |
| 3200431 | 7/1983 | Fed. Rep. of Germany | 568/639 |
| 2460283 | 2/1981 | France | 568/639 |
| 01193839 | 11/1984 | Japan | 568/639 |
| 1415945 | 12/1975 | United Kingdom | 568/639 |

OTHER PUBLICATIONS

Gazz. Chim. Ital. 86, 1956, pp. 1246–1257.
FACS, 59, 1937, pp. 2578–2580, Suter et al.
J. Org. Chem., 27, 1962, pp. 4098–4101, Randall et al.
J. Am. Chem. Soc., 74, p. 5782, 1952, Kornblum et al.

*Primary Examiner*—Werren B. Lone

*Attorney, Agent, or Firm*—Kevin T. Mansfield; Edward M. Roberts

[57] ABSTRACT

The invention relates to a novel process for preparing chlorodiphenyl ethers of the formula I

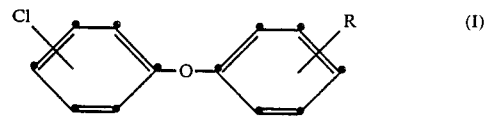

in which R is hydrogen or chlorine, which comprises heating a material of the formula III

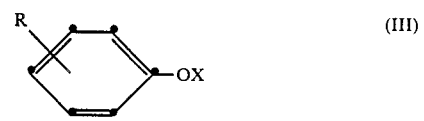

in which X is one equivalent of an alkali metal or alkaline earth metal ion and R is as defined above, in an excess of a dichlorobenzene of the formula II

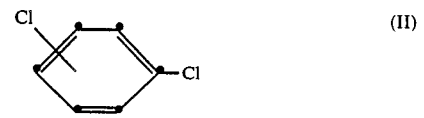

in the presence of a copper catalyst and of an aprotic solvent as cocatalyst at temperatures of 120°–220° C.

14 Claims, No Drawings

PROCESS FOR PREPARING CHLORINATED DIPHENYL ETHERS

The invention relates to a novel process for preparing chlorodiphenyl ethers.

Chlorinated diphenyl ethers are useful chemical intermediates in the pharmaceutical and crop protection industry (for example EP-A-No. 0,051,235, EP-A-No. 0,065,485 and EP-A-No. 126,430). In addition, chlorodiphenyl ethers have also been proposed as growth regulators (U.S. Pat. No. 4,124,370) or hydraulic oils (U.S. Pat. No. 3,371,120, U.S. Pat. No. 3,472,782).

To prepare diaryl ethers, in particular diphenyl ethers, a series of different methods are known. An advantageous method is the so-called Ullmann reaction (cf. Krauch-Kunz, Reaktionen der organischen Chemie [Reactions of organic chemistry], Dr. A. Hüthig Verlag Heidelberg, 1976, p. 320). This reaction consists in reacting alkali metal phenolates with aryl halides in the presence of copper or copper compounds as catalyst at elevated temperature.

The Ullmann reaction is in turn known in a series of different embodiments. In general, the Ullmann reaction requires the presence of an activated haloaromatic, such as iodobenzene or bromobenzene. According to Houben-Weyl (Methoden der organischen Chemie [Methods of organic chemistry], G. Thieme Verlag Stuttgart 1965, vol. VI.3, p. 86), bromine compounds (aryl bromides) are more reactive than the corresponding chlorine compounds.

Thus the preparation of 2-, 3- and 4-chlorodiphenyl ether from 2- or 3-chloroiodo or bromobenzene has been disclosed (J. Amer. Chem. Soc.: 59 [1937] 2578 and Gazz. Chim. Ital.: 86 [1956] 1248). Bromobenzene or iodobenzene, as well as the mixed chlorobromo- or chloroiodobenzenes, are less readily available than chlorobenzene or the isomeric dichlorobenzenes.

Various variants of the Ullmann reaction have therefore been proposed on the basis of reacting the basically less reactive dichlorobenzenes with phenoate or chlorophenolate. In U.S. Pat. No. 3,472,782 and U.S. Pat. No. 3,371,120, 1,4-dichlorobenzene is reacted with 3-chlorophenolate at 165° C. under CuCl/KI catalysis to give 3,4'-dichlorodiphenyl ether.

EP-A-No. 0,051,235 proposes improving the Ullmann catalyst by using basic copper carbonates or copper salts of lower aliphatic carboxylic acids and excess phenol. Neither this process nor the aforementioned processes are satisfactory in respect of yield, reaction control and reaction time. For instance, we have found that 4-chlorophenolate reacts with 1,3-dichlorobenzene at 150° C. over a copper (CuO) catalyst to form 3,4'-dichlorodiphenyl ether in a yield of only 10–20% even after 24 hours of reaction.

Furthermore, it is known that if dimethylformamide is used as solvent the Ullmann reaction can be advantageously carried out with activated halobenzenes. The reaction has been described inter alia of nitropenolates with chloronitrobenzenes to give the corresponding dinitrodiphenyl ethers (J. Org. Chem.; 27 [1962] 4098). Elsewhere (J. Amer. Chem. Soc. 74 [1952] 5782) it is pointed out that the use of less reactive halobenzenes as educts and dimethylformamide as solvent does not improve the known low product yields.

This is in agreement with our own studies, where, by reacting 1,3-dichlorobenzene with 4-chlorophenolate over a copper catalyst it was found that, in addition to the low conversions to 3,4'-dichlorodiphenyl ether, this ether additionally reacts further with 4-chlorophenolate still present in the reaction mixture in the form of chlorine/phenolate replacement to give oligomeric (preferably trimeric and tetrameric) ethers.

It is thus an object of the present invention to provide a process for synthesizing chlorinated diphenyl ethers where the basically less reactive dichlorobenzenes can be reacted with phenolate or chlorophenolate in high yields and high selectivity to give the desired products.

This object is achieved according to the invention with a process for preparing chlorodiphenyl ethers of the formula I

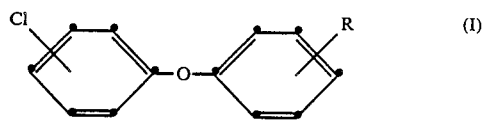

in which R is hydrogen or chlorine, which comprises heating a phenolate of the formula III

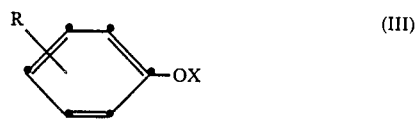

in which X is one equivalent of an alkali metal or alkaline earth metal ion and R is as defined above, in an excess of a dichlorobenzene of the formula II

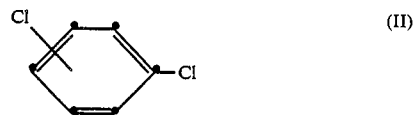

in the presence of a copper catalyst and of an aprotic solvent as cocatalyst at temperatures of 120°–220° C.

Aprotic solvents are inter alia: sulfolane, butyronitrile, amines, such as di-n-butylamine, anilines, such as aniline, methylaniline and dimethylaniline, acetonitrile, propionitrile, pyridines, dimethylformamide, dimethyl sulfoxide, diethylene glycol dimethyl ether, 1,2-dimethoxyethane, hexamethylphosphoramide, 1-methylpyrrolid-2-one, dimethylacetamide, benzonitrile, formamide, ethylene carbonate, propylene carbonate, N-methylformamide and the like.

Preference is given to dimethylformamide, dimethylacetamide, dimethyl sulfoxide and 1-methylpyrrolid-2-one.

The reaction is preferably carried out under atmospheric pressure. In the case of low-boiling cocatalysts or if elevated reaction temperatures are desired, the reaction can also be carried out under superatmospheric pressure, in particular under pressures of up to 5 bar. However, the pressure is not critical; it is also possible to work under reduced pressure, in particular down to 0.5 bar.

Preference is given to temperatures of 130° to 190° C., in particular 140° to 170° C. Advantageously it is possible to work under atmospheric pressure at somewhat below the boiling point of the reaction mixture. The boiling temperature is primarily determined by the dichlorobenzene of the formula II which is present in excess and by the pressure. Particular preference is thus given to the temperature range of 150° to 170° C.

The amount of aprotic solvent added for use as cocatalyst can range from 0.3 to 300 mol % (based on the phenolate), in particular from 5 to 100 mol %, preferably from 20 to 40 mol %, and is affected to a certain extent by the other process parameters (temperature, cocatalyst, structure of catalyst, ratio of educts III and II etc.). The optimal amount of cocatalyst in a particular case can be determined by simple experiments. This amount, if dimethylformamide or dimethylacetamide are used (at 150° C. reaction temperature with CuO as catalyst and a molar ratio of II:III=9:1), is about 30 mol %.

Specific Ullmann catalysts include inter alia: metallic copper (copper bronze, possibly activated by treatment with an acetonic iodine solution and hydrochloric acid), CuI, CuBr, CuBr$_2$, CuCN, Cu(NO$_3$)$_2$, CuSO$_4$, CuCl, CuCl$_2$, Cu(OH)$_2$, CuCO$_3$·Cu(OH)$_2$, Cu(OCOCH$_3$)$_2$, Cu$_2$O or CuO as well as the EP 51,245 Cu carbonates and salts of lower aliphatic carboxylic acids. CuO is suitable for use as catalyst in a particularly advantageous manner.

The catalyst can be recovered after the reaction is ended and be reused.

The advantageously usable amount of Ullmann catalyst in a particular case ranges from 0.5 to 100 mol % (based on phenolate III), preferably from 1 to 50 mol %, in particular from 1 to 5 mol %. The other process parameters, such as temperature, cocatalyst, ratio of educts etc., have an effect on the optimal amount of Ullmann catalyst in a particular case. The optimal amount for a particular case can be determined by experiment with respect to the desired space-time yield. The amount is preferably 1 to 2 mol % if CuO is used (at 150° C., dimethylformamide or dimethylacetamide as cocatalyst and a molar ratio of II:III=9:1).

In the process according to the invention, the dichlorobenzene of the formula II is used in excess as solvent. Advantageously, the ratio II:III is 3:1 to 15:1, in particular 5:1 to 12:1.

Whereas in the prior art processes the phenolate III is first prepared in a separate process step in another solvent, according to the invention the phenolate can be formed directly with NaOH or KOH and the phenol of the formula IV in the dichlorobenzene II used as solvent.

The salt formation in accordance with the following formula

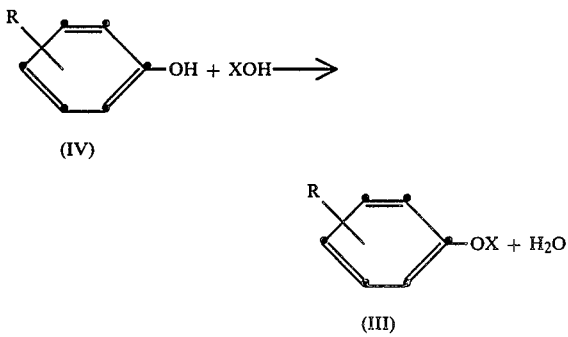

is advantageously carried out at room temperature or slightly elevated temperatures (up to 120° C.). This is followed by heating to the boil and removal of the water of reaction formed in the course of salt formation with a water separator. This process step is preferably carried out under reduced pressure. In the case of solid dichlorobenzenes of the formula (II), the addition of an azeotropic entraining agent, such as toluene or xylene, can be advantageous so as to prevent the compound of the formula (II) from crystallizing out during the removal of water. However, the use of an entraining agent is not absolutely necessary; crystalization can also be prevented by slightly heating the water separator. The salt of the formula III thus obtainable, after addition of Ullmann catalyst and cocatalyst (although the latter can also be added earlier to the reaction mixture at the salt formation stage), reacts at the appropriate reaction temperature with the dichlorobenzene (II), which is present in excess, in the previously described manner to give the product of the formula I.

The sodium hydroxide or potassium hydroxide required as base can be added in solid form, but is advantageously added as monohydrate or in concentrated aqueous solution. Excess water is removed together with the water freed in the course of the reaction by separating out of the reaction mixture. Compared with the prior art processes, salt formation in dichlorobenzene II used as solvent for the Ullmann reaction is advantageous since, according to the invention, no change of solvent is necessary between the two stages.

Using the process according to the invention, chlorodiphenyl ethers of the formula I can be prepared in high yield and high selectivity at relatively low reaction temperatures in a relatively short reaction time. Under the abovementioned reaction conditions, the reaction to obtain I is virtually complete in from 4 to 15 hours.

In a particularly advantageous manner, the reaction according to the invention is suitable for preparing 3,4'-dichlorodiphenyl ether from 1,3-dichlorobenzene and 4-chlorophenol or 1,4-dichlorobenzene and 3-chlorophenol. It is known that, for example, owing to the meta-substitution in 1,3-dichlorobenzene, the electron-attracting effect of the two chlorine substituents on each other is only very small and that consequently, for Ullmann reactions, 1,3-dichlorobenzene cannot be regarded as an activated halobenzene. Similar considerations apply to 1,2-dichlorobenzene and to a special degree also to 1,4-dichlorobenzene. Although the electronegative effect of the second chlorine atom bonded in the 2- or para-position exerts a very weak activating effect on the reactive Ullmann centre, this effect is weakened by an electron-donating effect due to mesomerism to such an extent that even 1,2- and 1,4-dichlorobenzenes cannot be regarded as activated educts for the purposes of an Ullmann reaction. Consequently, it is extremely surprising that by using an Ullmann educt (dichlorobenzene II) as solvent in combination with a cocatalyst the diphenyl ethers I are preparable in high yield and selectivity in a short reaction time and at a low reaction temperature.

The following Examples illustrate the invention.

EXAMPLE 1

3,4'-Dichlorodiphenyl ether 80 g of 50% sodium hydroxide are added to a solution of 128.1 g (1.0 mol) of 4-chlorophenol in 1325 g (9 mol) of 1,3-dichlorobenzene and 27 g (0.3 mol) of dimethylacetamide.

The mixture is heated with stirring under a low vacuum (600 mbar), and starting at an internal temperature of about 110° C. water starts to separate off. The internal temperature is continuously raised to 150° C.

1.2 g of CuO are then added to the reaction mixture, and the reaction mixture is allowed to react to completion with vigorous stirring at an internal temperature of 150° C. under atmospheric pressure.

After cooling down, the mixture is diluted with 200 ml of water, brought to pH 12 with NaOH and filtered through Hyflo, the aqueous phase is separated off, and the organic phase is worked up by distillation under a high vacuum.

This gives 190 g (80%) of the title compound of the formula

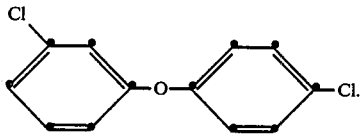

EMAMPLE 2

3,4'-Dichlorodiphenyl ether 80 g (1 mol) of 50% sodium hydroxide are added to a solution of 128.1 g (1 mol) of 3-chlorophenol in 1325 g (9 mol) of 1,4-dichlorobenzene and 27 g (0.3 mol) of dimethylacetamide.

The mixture is heated with stirring under a low vacuum, and the water is separated off (to simplify matters, toluene can be added as an entraining agent for water). 1.2 g of CuO are then added to the reaction mixture, and with vigorous stirring the reaction is completed at an internal temperature of 150° C. under atmospheric pressure. Aqueous working up and high-vacuum distillation of the organic phase (analogously to Example 1) gives 180 g (75%) of the title compound.

EXAMPLE 3

2,4'-Dichlorodiphenyl ether 80 g (1 mol) of 50% sodium hydroxide are added to a solution of 128.1 g (1 mol) of 4-chlorophenol in 1470 g (10 mol) of 1,2-dichlorobenzene and 40 g (0.45 mol) of dimethylacetamide.

Water is separated off with stirring under a low vacuum (analogously to Example 1).

2,3 g of CuO are then added to the reaction mixture, which is then made to react with stirring at 150° C. under atmospheric pressure. Aqueous working up and high-vacuum distillation (analogously to Example 1) gives 190 g (80%) of the title compound of the formula

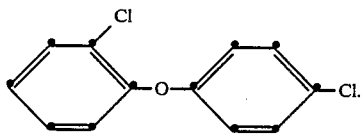

What is claimed is:

1. A process for preparing chlorodiphenyl ethers of the formula I

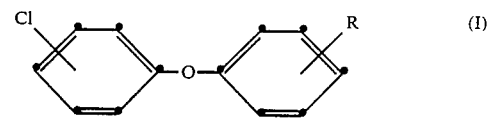

in which R is hydrogen or chlorine, which comprises heating a phenolate of the formula III

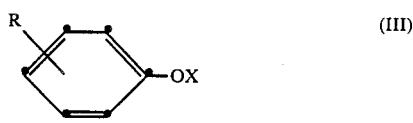

in which X is one equivalent of an alkali metal or alkaline earth metal ion and R is as defined above, in an excess comprising 3–15 moles of a dichlorobenzene of the formula II

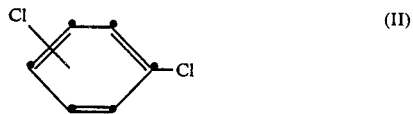

in the presence of a copper catalyst and 0.003 to 3 moles of an aprotic dipolar solvent as cocatalyst at temperatures of 120°–220° C.

2. A process according to claim 1 for preparing 3,4'-dichlorodiphenyl ether I from 1,3-dichlorobenzene (II) and sodium 4-chlorophenolate (III).

3. A process according to claim 1, wherein the phenolate of the formula III is prepared by reacting a chlorophenol of the formula IV

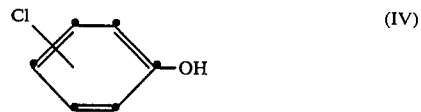

with XOH, where X is one equivalent of an alkali metal or alkaline earth metal ion, in dichlorobenzene (II) in the absence or presence of an aprotic solvent as cocatalyst, and the water present in the reaction mixture is separated out at elevated temperatures, at atmospheric or under reduced pressure.

4. A process according to claim 1, wherein the Ullmann reaction is carried out at temperatures of 130°–190° C.

5. A process according to claim 1, wherein the reaction is carried out at 140°–170° C.

6. A process according to claim 1, wherein the cocatalyst is selected from sulfolane, butyronitrile, di-n-butylamine, aniline, methylaniline, dimethylaniline, acetonitrile, propionitrile, pyridine, dimethylformamide, dimethyl sulfoxide, diethylene glycol dimethyl ether, 1,2-dimethoxyethane, hexamethylphosphoramide, 1-methylpyrrolid-2-one, dimethylacetamide, benzonitrile, formamide, ethylene carbonate, propylene carbonate or N-methylformamide.

7. A process according to claim 1, wherein the cocatalyst is selected from dimethylformamide, dimethylacetamide, dimethyl sulfoxide or 1-methylpyrrolid-2-one.

8. A process according to claim 1, wherein the cocatalyst content is 5 to 100 mol %.

9. A process according to claim 1, wherein the cocatalyst content is 20 to 40 mol %.

10. A process according to claim 1, wherein the copper catalyst used is metallic copper (copper bronze, unactivated or activated by treatment with an acetonic iodine solution and hydrochloric acid), CuI, CuCl, $CuCl_2$, CuBr, $CuBr_2$, CuCN, $Cu(NO_3)_2$, $CuSO_4$, $Cu(OH)_2$, $CuCO_3 \cdot Cu(OH)_2$, $Cu(OCOCH_3)$, $Cu_2O$ or CuO.

11. A process according to claim 1, wherein the copper catalyst content is 0.5–100 mol %.

12. A process according to claim 1, wherein the copper catalyst content is 1–50 mol %.

13. A process according to claim 1, wherein the copper catalyst content is 1–5 mol %.

14. A process according to claim 1, wherein the ratio of educts II:III ranges from 5:1 to 12:1.

* * * * *